United States Patent [19]

Wuchinich

[11] Patent Number: 5,358,505
[45] Date of Patent: Oct. 25, 1994

[54] TAPERED TIP ULTRASONIC ASPIRATION METHOD

[75] Inventor: David G. Wuchinich, New York, N.Y.

[73] Assignee: Sonokinetics, Inc., Hoboken, N.J.

[21] Appl. No.: 81,580

[22] Filed: Jun. 22, 1993

Related U.S. Application Data

[60] Division of Ser. No. 964,570, Oct. 21, 1992, Pat. No. 5,221,282, which is a continuation-in-part of Ser. No. 706,669, May 29, 1991, abandoned.

[51] Int. Cl.$^5$ .................................... A61B 17/56
[52] U.S. Cl. .................................... 606/99
[58] Field of Search .......... 606/46, 70, 92, 99; 604/22; 128/898, 24 AA

[56] References Cited

U.S. PATENT DOCUMENTS

| | | | |
|---|---|---|---|
| 2,742,076 | 4/1956 | Klein | 29/427 |
| 3,401,446 | 9/1968 | Obeda et al. | 156/344 X |
| 3,526,219 | 9/1970 | Balamuth | 128/2 |
| 3,589,363 | 6/1971 | Banko et al. | 128/276 |
| 3,614,484 | 10/1971 | Shoh | 310/8.2 |
| 3,683,736 | 8/1972 | Loose | 264/25 X |
| 3,809,977 | 5/1974 | Balamuth | 318/116 |
| 3,906,954 | 9/1975 | Baehr et al. | 604/27 |
| 4,063,557 | 12/1977 | Wurchinich et al. | 128/276 |
| 4,203,444 | 5/1980 | Bonnell et al. | 128/276 |
| 4,223,676 | 9/1980 | Wuchinich et al. | 128/276 |
| 4,248,232 | 2/1981 | Engelbrecht et al. | 182/24 AA |
| 4,316,465 | 2/1982 | Dotson, Jr. | 604/22 |
| 4,425,115 | 1/1984 | Wuchinich | 604/22 |
| 4,428,748 | 1/1984 | Peyman et al. | 604/22 |
| 4,493,694 | 1/1985 | Wuchinich | 604/22 |
| 4,504,264 | 3/1985 | Kelman | 604/22 |
| 4,516,398 | 6/1988 | Wuchinich | 604/22 |
| 4,603,694 | 8/1986 | Wheeler | 604/22 |
| 4,609,368 | 9/1986 | Dotson, Jr. | 604/22 |
| 4,643,717 | 2/1987 | Cook et al. | 604/22 |
| 4,702,236 | 10/1987 | Tarabichy et al. | 128/92 V |
| 4,732,156 | 3/1988 | Nakamura | 128/660 |
| 4,747,820 | 5/1988 | Hornlein et al. | 604/22 |
| 4,748,985 | 6/1988 | Nagasaki | 128/660 |
| 4,750,488 | 6/1988 | Wuchinich et al. | 128/303 R |
| 4,750,902 | 6/1988 | Wuchinich et al. | 604/22 |
| 4,756,309 | 7/1988 | Sachse et al. | 606/180 X |
| 4,828,052 | 5/1989 | Duran et al. | 175/55 |
| 4,834,102 | 5/1989 | Schwarzchild et al. | 128/662.06 |
| 4,838,853 | 6/1989 | Parisi | 604/22 |

(List continued on next page.)

FOREIGN PATENT DOCUMENTS

| | | |
|---|---|---|
| 121491 | 10/1984 | European Pat. Off. . |
| 243298 | 10/1987 | European Pat. Off. . |
| 203229 | 10/1983 | Fed. Rep. of Germany .......... A61B 17/32 |

(List continued on next page.)

OTHER PUBLICATIONS

Krawitt et al., Ultrasonic Aspiration of Prostate, Bladder Tumors and Stones, *Urology*, 30.6 (1987) pp. 578–580.

(List continued on next page.)

*Primary Examiner*—William E. Kamm
*Attorney, Agent, or Firm*—Pennie & Edmonds

[57] ABSTRACT

A method for the melting and removal of thermoplastic prosthetic implant cement through the use of an aspirating ultrasonic surgical device is provided. The instrument defines a centrally located bore which expands in diameter from a surgical tip in the direction of aspirant flow for a length equal to at least ¼ the wavelength corresponding to the resonant frequency of the device so as to prevent blockage by solidified cores of cement. Alternatively, the bore expands from a first uniform diameter extending from the tip end to a second uniform diameter. A compound taper at the tip end minimizes contact between the outer surface of the tube at the tip end. A novel transducer cooling system is provided by incorporating a thermally conductive, electrically insulating material between the piezoelectric crystal (which generates heat as a byproduct) and a hollow metal bolt which defines a central bore through which cooling irrigant flows to conductively remove heat generated by the crystal.

12 Claims, 6 Drawing Sheets

U.S. PATENT DOCUMENTS

| | | | |
|---|---|---|---|
| 4,846,161 | 7/1989 | Roger | 128/92 V |
| 4,846,790 | 7/1989 | Hornlein et al. | 604/22 |
| 4,873,969 | 10/1989 | Huebsch | 128/92 R |
| 4,880,011 | 11/1989 | Imade et al. | 128/662.06 |
| 4,881,761 | 11/1989 | Hornlein et al. | 285/239 |
| 4,936,281 | 6/1990 | Stasz | 128/660.03 |
| 4,979,952 | 12/1990 | Kubota et al. | 606/169 |
| 4,989,588 | 2/1991 | Kubota et al. | 604/22 |
| 5,019,083 | 5/1991 | Klapper et al. | 606/99 |
| 5,027,792 | 7/1991 | Moyer | 606/46 |
| 5,045,054 | 9/1991 | Hoop et al. | 606/99 |
| 5,062,827 | 11/1991 | Wiksell | 128/24 AA |
| 5,151,099 | 9/1992 | Young et al. | 606/92 |
| 5,167,619 | 12/1992 | Wuchinich | 606/99 |

FOREIGN PATENT DOCUMENTS

| | | |
|---|---|---|
| 2614524 | 11/1988 | France . |
| 9010423 | 9/1990 | PCT Int'l Appl. . |
| 1371335 | 10/1974 | United Kingdom . |

OTHER PUBLICATIONS

Richmond et al., Evaluation of the Histopathology of Brain Tumor Tissue Obtained by Ultrasonic Aspiration, *Neurosurgery*, 13:4 (1983), pp. 415–419.

Malloy et al., Endoscopis Ultrasonic Aspiration of the Prostate, Bladder Tumors and Stones, Journal of Urology Supplement, May 1989.

Epstein et al., Surgical Managmenet of Extensive Intramedullary Spinal Cord Astrocytoma in Children, Concepts in Pediatric Neurosurgery, 2, (1982) pp. 29–44.

Sternlieb et al., Ultrasonic Restoration of Severely Calcified Aortic Valve, *The Lancet*, Aug. 20, 1988, p. 446.

Caspar, Current Development of Instrumentation for Arthroscopy, *Clinics in Sports Medicine*, 6:3 (1987), pp. 626–627.

Johnson, Arthroscopic Surgery: Principles and Practice (3rd Edition), Verlag, Springer (1986), pp. 244–245.

Brochure, Endo-Urology-A Breakthrough in Ultrasonic Lithotripsy, Karl Storz Endoscopy America, Inc. (1984).

Brochure, Instruments and Apparatus for Lithotripsy, Richard Wolf GmbH, Knittlinger, West Germany (1984).

Brochure, Percutaneous Low Pressure Universal Nephroscope, Richard Wolf, Knittlinger West Germany (1984).

Goliamina, "Ultrasonic Surgery", Proceedings of the Eighth Int'l. Cong. on Acoustics, London, 1974, pp. 63–69.

Klapper and Caillouette, "The Use of Ultrasonic Tools in Revision Arthoplasty Procedures", 20:3 Contemporary Orthopaedics, pp. 273–279 (Mar. 1990).

Ensminger, *Ultrasonics: Fundamentals, Technology, Applications*, pp. 462–467, Marcel Dekker Inc. (1988).

Brochure, *Sonic Surgery System*, Quintron, Inc.

Malloy et al., Transurethral Ultrasonic Aspiration of the Prostrate, A.U.A., May 1989.

X. Zhou, et al., Effect of Press-Fit Femoral Stems on Strains in the Femur, 5 J. Arthroplaty 71 (1990).

J. Schwartz, Jr., et al., Femoral Fracture During Non-Cemented Total Hip Arthroplasty, 71-A J. Bone & Joint Surgery 1135 (1989).

H. Cameron, Proximal Femoral Osteotomy in Difficult Revision Hip Surgery: How to Revise the Unrevisable, 18 Contemp. Orthopaedics 565 (1989).

R. Karpman, et al., The Lithotriptor and Its Potential Use in the Revision of Total Hip Arthroplasty, 16 Orthopaedic Rev. 81 (1987).

J. Moreland, et al., The Window Technique for the Removal of Broken Femoral Stems in Total Hip Replacement, 212 Clinical Orthopaedics and Related Research 245 (1986).

S. McClelland, et al., Atraumatic Removal of a Well-Fixed Porous Ingrowth Hip Prosthesis, 15 Orthopaedic Rev. 75 (1986).

P. Lin, Posterior Lumbar Interbody Fusion Technique: Complications and Pitfalls, 193 Clinical Orthopaedics and Related Research 90 (1985).

W. Harris, et al., A New Technique for Removal of Broken Femoral Stems in Total Hip Replacement, 63-A J. Bone & Joint Surgery 843 (1981).

Richards Mfg. Co., Orthopedic Catalog (1981).

E. Weis, Jr., A Sonic Tool for Spinal Fusion, 8 Orthopedic Clinics of North Am. 43 (1977).

De Puy Inc., Catalog (1966).

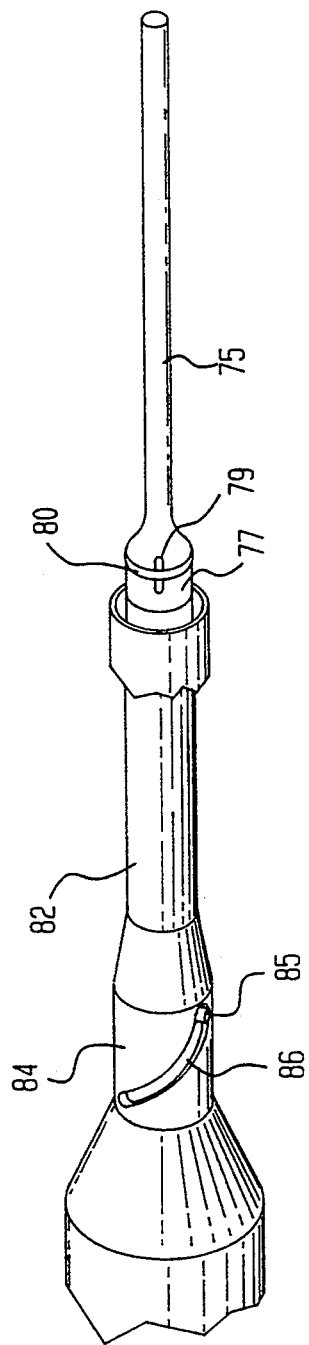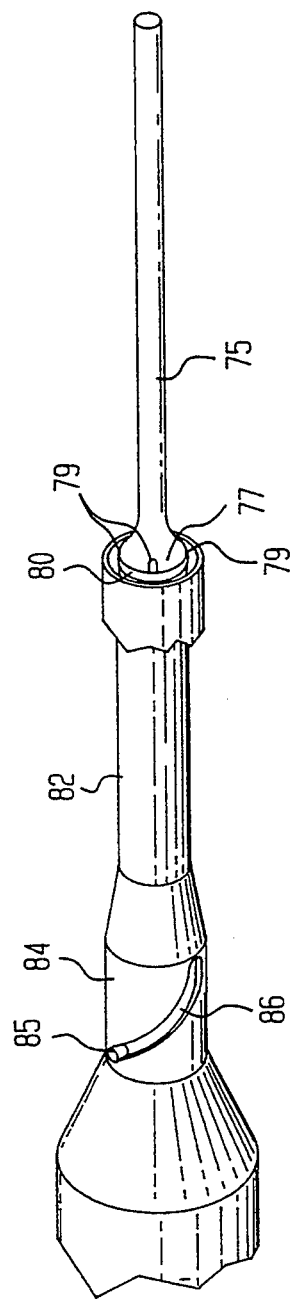

TAPERED TIP ULTRASONIC ASPIRATION METHOD

CROSS REFERENCE TO RELATED APPLICATIONS

This application is a division of application Ser. No. 07/964,570 filed Oct. 21, 1992, now U.S. Pat. No. 5,221,282, which is a continuation-in-part of application Ser. No. 07/706,669 filed May 29, 1991, abandoned.

TECHNICAL FIELD

This invention relates in general to an ultrasonic surgical apparatus, in particular to novel aspirator tips for ultrasonic aspirators.

BACKGROUND OF THE INVENTION

The use of ultrasonically vibrated slender hollow metal tubes for cutting and removing biological tissue is well known. U.S. Pat. Nos. 3,589,363, 4,063,557, 4,223,676, 4,425,115, 4,493,694, 4,516,398, 4,750,902, and 4,750,902 disclose devices which utilize such tubes for the removal of such tissue.

In the prior art, the end of the slender hollow metal tube is vibrated axially by means of an ultrasonic transducer. When the tip is brought into contact with tissue, cavitation or mechanical shearing separates a core-like section of tissue which is then aspirated into the bore of the hollow tip by means of a vacuum provided therein. A separate suction pump which is connected to the tip provides the required vacuum. The tissue requiring excision such as, for example, brain neoplasms or prostatic tissue is usually soft and compliant. Tissue cores comprised of soft matter such as this flows easily through the tip and the tubing to which it is usually connected. Because of the compliance of the tissue, bends intentionally present in parts of the tip and tubing do not impeded the flow of such cores to the collection vessel. Generally, the diameter of the tip and associated tubing is of a constant diameter or cross section.

It is also known by U.S. Pat. No. 4,248,232 to utilize an ultrasonic tool for dissolving the bond between nested components such as a bone prosthesis and surrounding bone which are cemented together by a plastic layer. The vibrating tool, which in one embodiment may be a hollow probe that includes a thin tubule, is pressed into the bone cement. After the cavity of the tubule is filled, the probe is pulled out of the bone cement and the plastic is removed from the cavity. This patent also suggests that a window can be provided in the wall of the tubule so that bone cement traveling up the cavity can be continuously extruded and that a vacuum device can be connected to the window to continuously extract the plastic during use of the tool.

A new application of ultrasonic surgical cutting technology using an endoscopic ultrasonic aspirator has recently been developed by Wuchinich and is disclosed in U.S. patent application Ser No. 07/529,029 filed May 25, 1990. This aspirator effectively removes thermoplastic cement adherent to bone surfaces during prosthesis revisional surgery. A particularly useful application for the technology is in the removal of methylmethacrylate from the femoral canal during hip revision surgery. A hollow metal tip is ultrasonically vibrated at a sufficient amplitude and frequency so as to melt thermoplastic surgical cement it contacts. Vacuum within the tip draws the melted cement into its bore as well as a large quantity of water utilized to cool the surgical site and protect against heat necrosis of adjacent cortical bone. Irrigation flow rates ranging from 100 to 500 cubic centimeters of water per minute are utilized for this protective purpose. As the melted cement is aspirated into the tip, it cools and recrystallizes so as to form a solid core. Irrigating saline enhances the rate of re-solidification within the bore of the tip.

Within a few millimeters of the surgical tip's cutting end, the cement has become a solid, rigid cylinder whose cross section duplicates that of the tip's bore. The length of these cylinders vary with the penetration depth of the tip into the cement, but can easily reach 10 to 20 times the diameter of the bore. Because the core, upon re-solidification, will substantially reproduce the configuration of the tip's bore, curves and irregularities, (such as recesses, burrs, protrusions and cavities), the internal surface of the tip may mold a curved or irregular core of plastic which may become an obstruction to the passage of the cores to the collection vessels. Once an initial core forms an obstruction, successive cores may quickly cause a complex blockage. Clearing such a blockage distracts the surgeon, prolongs the surgery and necessarily requires extension of anesthesia.

As a normal byproduct of ultrasonic transducer operation, a considerable amount of heat is generated. Removal of cement from the walls of a bone canal requires a prolonged operation of a transducer. The associated prolonged heat thereby generated may lead to cracks within, or a loosening of a structure housing the transducer.

The effectiveness of conventional ultrasonic devices for cutting and aspirating thermoplastic cement material can be further reduced or even neutralized by the adhesion of recrystallized cement to the exterior surface of the vibrating tip. Specifically, when the outer surface of the tip penetrates the cement to perform excavation, the cement may resolidify thereon even during brief periods of non-vibration. The resulting solid layer of cement material envelopes the tip and prevents reinitiation of tip vibration. If the static load imparted by the resolidified layer exceeds the power capacity of the electrically operated ultrasonic generator while the tip is embedded in the cement material, vibration will cease and the use of manual tools to dislodge the tip from the cement may be required.

Another undesirable load on the ultrasonic generator is that in addition to delivering the vibratory power needed to melt the cement material that is to be removed through the bore, it must also supply sufficient power to melt any cement material contacting the outer tip surface as it enters the cement. Any additional power thus consumed in melting the cement contacting the outer tip surface is converted directly into heat and results in an undesirable elevation of temperature at the excavation site. It has been found that undesirable power consumption is greatest for those tip surface configurations which utilize a uniform diameter or a diameter that progressively increases in the direction of the handpiece. Uniform or progressively tapered outer surface configurations also tend to impede the flow of cooling fluid to the excavation site because melted cement surrounding the outer tip surface restricts the flow to the end of the tip. Consequently, unwanted elevations in temperature are produced where the cement is being withdrawn, resolidification of the cement within the bore of the tip is retarded, and those portions of the tip most subject to the cyclic stress of vibration receive little or no cooling.

What is needed, therefore, is an ultrasonic surgical instrument for the removal of prosthetic cement which includes a hollow tip which is highly resistant to blockages caused by core jams, which minimizes the power required to penetrate the cement, which provides cooling fluid with access to the excavation site, and which reduces the likelihood of tip removal problems. What is also needed is an ultrasonic surgical instrument which includes an ultrasonic transducer which may provide prolonged operating time without suffering failure due to excessive heat production.

SUMMARY OF THE INVENTION

Now in accordance with the present invention, an aspirating ultrasonic surgical instrument for the removal of prosthetic cement is provided. The working aspiration tip of this instrument includes a hollow surgical tube defining a centrally located bore which is designed to resist blockage from cement cores. Also an ultrasonic transducer capable of prolonged operation without suffering heat related failures is provided in the instrument.

The hollow surgical tube includes a generally central bore and, at one end, an open tip having a circumferential annulus for contacting and imparting ultrasonic vibrations to the cement. These vibrations melt the cement for removal by aspiration. At the opposite end of the tip, a transducer contacting surface is provided for receiving ultrasonic vibrations generated by the ultrasonic transducer. The bore of the hollow tube defines, beginning at the tip, a monotonically increasing cross-section. The hollow tube is provided with ultrasonic vibration for melting thermoplastic prosthetic cement by means of an ultrasonic transducer affixed to the transducer contacting surface of the hollow tube. The transducer also defines a centrally located bore which is adjacent and contiguous with the bore defined by the hollow tube. Melted material removed by the ultrasonically vibrating annulus is aspirated through the contiguous bores defined by the hollow tip and the transducer by means of suction provided by a vacuum pump. The pump is connected by tubing to a vacuum fitting located at an end of the transducer opposite to the tube contacting end.

The transducer of the present invention includes a piezoelectric crystal which produces, upon excitation by a suitable source of alternating current, a pre-determined resonant frequency which allows the device to melt thermoplastic prosthetic cement. The wavelength corresponding to the resonant frequency is determined in order to select the proper length for an efficient tube for conducting the ultrasonic vibrations to the cement. It has been found that a tube length of $2n + \frac{1}{2}\lambda$ where n is zero or a positive integer provides for an efficient conduction of the ultrasonic vibration provided by the piezoelectric crystal.

When the present invention is utilized for cement removal, the preferred range of peak to peak tip excursion is from 50 to 500 microns ($10^{-6}$ m) and the preferred range of frequencies of this vibration is from 10 to 50 kHz (1000 cycles per second).

In one embodiment of the present invention, the hollow metal tube includes a first section, contacting the transducer at one end, and a second section including the surgical tip, permanently joined thereto. Each section is preferably one quarter wavelength in length. Also, although the two sections may be unitary so as to form a one half wavelength resonator. The present invention requires a tip whose length is any integral multiple of a half wavelength.

The second section, which at one end includes the surgical tip and at an opposite end adjoins the first section, has a constantly increasing bore diameter from the tip to the end adjoining the first section. The cross section of the first section may either be uniform or continue to enlarge as its bore approaches the transducer. However, in any case, the cross sectional bore diameter of the first section should be at least as large as the largest bore diameter of the second section and should not decrease in diameter as the bore approaches the transducer contacting end.

A compound taper section is preferably formed on the surface of the tube proximate the tip end of the second section and comprises a first tapered portion increasing progressively in thickness towards the tip and a second tapered portion decreasing progressively in thickness towards the tip. The thickest regions of the first and second tapered sections are contiguous and together define a maximum thickness of the compound taper section which is from 50 to 500 percent of the diameter of the bore at the tip. The combined length of the tapered portions is from 2 to 100 percent of a quarter wavelength and the angles defined by exterior surfaces of the first and second tapered portions, as measured relative to a longitudinal axis of the tube, are in proportion to each other in a ratio varying from 1 and 100 percent.

In another embodiment, the bore defined by the first section is of a first uniform diameter and at least a portion of the bore defined by the second section is of a second uniform diameter which is less than the diameter of the first uniform diameter. The bore defined by said second section preferably includes an abrupt transition between the first and second uniform diameters located at a distance from the surgical tip of from 1 to 1000 percent of said second uniform diameter.

The present invention also provides a transducer which is especially configured and adapted so as to be resistant to thermal damage. The transducer comprises a hollow bolt and a cylindrical piezoelectric crystal defining a bore. The bolt includes a fixed cap at one end and an external threaded portion at an opposite end. Within the fixed cap, an internal thread is provided so as to enable the attachment of various hollow surgical tubes. The bolt is positioned within the bore defined by the crystal so that one end of the tube is adjacent to the cap. A nut is provided which mates with and engages the externally threaded portion of the bolt and is tightened so as to firmly affix the crystal between the cap and nut so that components of the transducer remain intact during the production of ultrasonic vibration.

The crystal includes electrodes located on its inner surface adjacent the bolt. The outer surface of the crystal is attached by a wire to a source of alternating current whose frequency is adjusted to the mechanical resonant frequency of the transducer. The present invention provides a means for removing the heat generated by the piezoelectric crystal during operation. Thus excessive heat which might ordinarily fracture the bolt or loosen the structure is avoided.

A thermally conductive, electrically insulating material is placed between the inner surface of the crystal and an adjacent outer surface of the bolt. Within the hollow bolt, cooling aspiration fluid supplied at the surgical site passes through its bore. As heat is liberated by the crystal, it is conducted through the thermally conductive material to the outer surface of the bolt. Heat is then conducted through the external surface of the bolt to the aspiration fluids flowing within the bore of the bolt. Aspiration fluids then safely conduct the heat away from the surgical device.

The thermally conductive electrically insulating material is selected so as not to impede required motion between the inner surface of the crystal, and the outer surface of the bolt. A suitable material, for example, is a powdered ceramic material such as boron nitride. Boron nitride has a thermal conductivity approximately equal to that of copper and is, at the same time, an electrical insulator. Additionally, the powdered form of boron nitride does not restrict the motion of the surfaces it contacts. While powdered graphite exhibits relatively poor dielectric properties in comparison to boron nitride, it does demonstrate adequate thermal conductivity. Thus, if electrical insulation between the crystals inner surface and the bolts outer surface is not required, powdered graphite can instead be used.

BRIEF DESCRIPTION OF THE DRAWINGS

FIGS. 8 and 9 are perspective views of the sheath in retracted and extended positions respectively.

DETAILED DESCRIPTION

Figure 1:
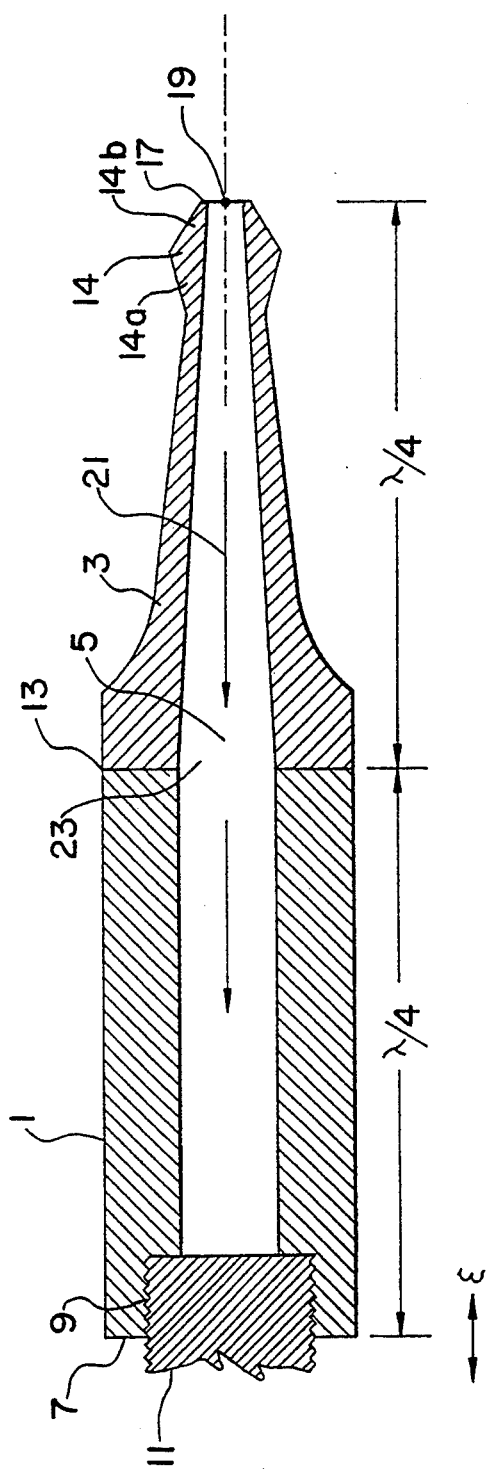
FIG. 1 is a side view, in cross section, of one embodiment of a hollow surgical tube according to the present invention.

As discussed above, the hollow surgical tube of the present invention allows a surgical ultrasonic aspirating device to melt and remove cement from bone cavities without experiencing core blockages. One embodiment of a hollow tube of the present invention is illustrated in FIG. 1. The hollow tube includes a first section 1 and a second section 3. Both sections define a contiguous central bore 5. The first section includes a transducer contacting end 7 at which is located an internal threaded portion 9. A hollow stud 11 positioned within this internal threaded portion is utilized to affix the transducer contacting end of the first section to the ultrasonic transducer wherein an adjacent internal threaded portion is located. At an end 13 opposite to the transducer contacting end, the first section of the hollow tube is permanently affixed to the second section.

The second section includes a surgical tip 15. The circumferential peripheral edge of the surgical tip defines an annulus 17 which contacts and conducts ultrasonic vibration into prosthetic cement. The bore diameter proximate to the tip end of the second section (point 19) increases as the first section of the hollow surgical tube is approached. Arrow 21 indicates both the direction of second section enlargement and the direction of aspiration flow during actual use of the device. As the interface of section one and two is approached from the surgical tip, the diameter of the second section reaches a maximum 23. In the embodiment of the present invention illustrated in FIG. 1, the bore diameter defined by the first section is equal to that of the largest diameter of the second section throughout its length. However, as discussed above, it is possible to increase bore diameter from the maximum 23 on (in the direction of aspiration flow (19) as long as:

a. there is no point from 23 to the collection vessel which defines a bore less than the bore diameter at 23, and b. there are no areas defining a decreasing bore diameter (relative to the aspiration flow).

In order to minimize power consumption requirements and to avoid restrictions in the flow of the cooling fluid, the surgical tube preferably includes a compound taper section 14 located proximate the cutting tip 15 of the second section 3. Compound taper section 14 is configured to permit irrigating fluid to reach the excavation site and to minimize the contact between the outer surface of the tip and the cement material surrounding the excavation site.

A first tapered portion 14a of section 14 increases progressively in thickness, circumference, or other defining cross sectional dimension towards the cutting tip. Thickness is measured from the interior wall of the tube and the surface of the tapered portion. In contiguous contact with the thickest portion of section 14a, a second tapered portion 14b then decreases progressively in thickness or other defining cross sectional dimension in the direction of the cutting tip.

Compound taper section 14 need only have a maximum thickness dimension d that is sufficient to allow irrigating fluid to reach the tip. This dimension preferably ranges from 50 to 500 percent of the diameter of the cutting bore. The combined length of the tapered sections preferably vary from 2 to 100 percent of a quarter wavelength, while the angles of the tapered surfaces, as measured relative to the axis of the tube itself, are preferably in proportion to each other in a ratio varying from 1 to 100 percent.

Although the present invention may also be constructed without a compound taper so as to have a tube with a constant diameter or an increasingly tapered cross sectional dimension, a compound taper is preferred because it minimizes the ultrasonic power required to penetrate the cement, provides access for cooling flow at the cutting tip, and reduces the likelihood of the tip becoming inextricably lodged in the cement. The compound taper 14 is preferably configured with a circular cross section. However, an oval or polygonal cross section might also be employed. Also, instead of being contiguous, tapered portions 14a and 14b may be bridged by a narrow intermediate portion of uniform thickness.

Figure 2:
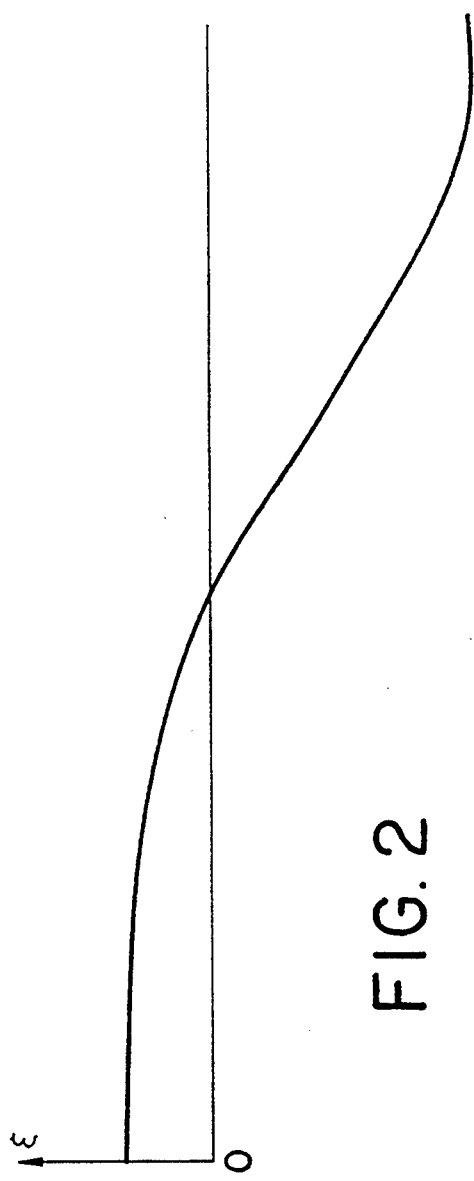
FIG. 2 is a wave diagram illustrating the relationship between tube length and wavelength thereby conducted.

The wave diagram (FIG. 2) illustrates that each section (first and second) is $\frac{1}{4}$ wavelength in length so that the entire surgical tube comprises a length of $\frac{1}{2}$ wavelength. Any integer multiple of $\frac{1}{2}$ wavelength may also be utilized.

As discussed above, the present invention requires a peak surgical tip excursion of from 50 to 500 microns ($10^{-6}$ m) and the preferred frequency range which provides such an excursion is from 10 to 50 kHz. The present invention utilizes a transducer which produces a frequency within this range, and the wavelength corresponding to the selected frequency is utilized to select the length of hollow tube required for efficient transmission of ultrasonic vibration produced.

The present invention also provides a tip whose length is any integral multiple of a half wavelength to provide greater "reach" for surgical access. To provide a device of adjustable length to accommodate a variety of bone canal depths, one embodiment of the present invention provides releasable joints between individual half-wave tube sections.

Sources of vacuum for surgical devices are well known. Surgical vacuum tubing provides a suitable conduit through which suction may be applied to the device through the vacuum fitting.

The bore of the second quarter wavelength section, whose surgical tip contacts the material to be melted and aspirated, is tapered in the embodiment shown in FIG. 1 so as to produce a monotonically increasing cross section. Although it is possible to extend this taper so as to include the first section, the prevention of core blockages is fully achieved by restricting the taper only in the second section.

Figure 10:
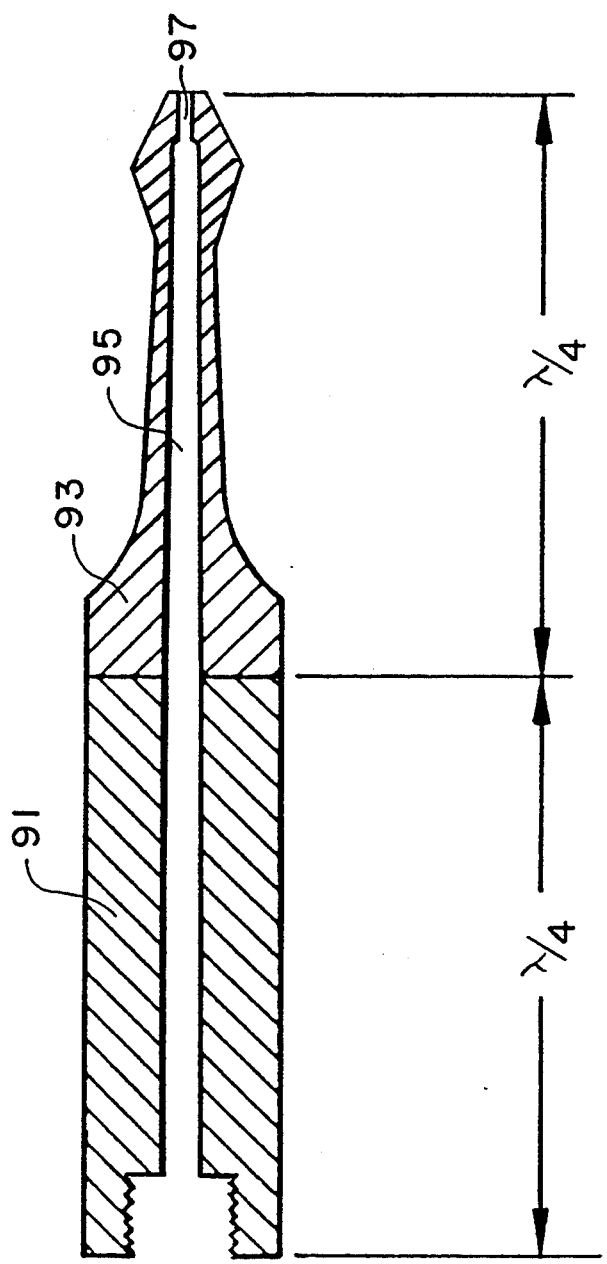
FIG. 10 is a side view, in cross section, of another embodiment of a hollow surgical tube according to the present invention.

In the embodiment of FIG. 10, the tube is modified so that the contiguous bore, which extends through first section 91 and second section 93, includes a first portion 95 having a uniform cross sectional dimension or diameter and a second portion 97 having a reduced cross sectional dimension or diameter portion located proximate the tip end of the second section. Portions 95 and 97 are contiguous and the transition between them is preferably abrupt for ease and economy of manufacture. However, the transition may also be graduated, if desired.

An abrupt reduction in bore cross section accomplishes materially the same objective as the tapered bore in the embodiment of FIG. 1 and may be made anywhere along the length of the tip. Preferably, however, the transition to the reduced bore cross section is located at a distance from the tip terminus equal to from 1 to 1000 percent of the bore diameter in the reduced cross section portion.

Since the bore of the tip increases, material aspirated through the end of the tip is immediately freed of surface contact and may proceed unimpeded to a collection jar as long as the bore of the hollow surgical tube, transducer and vacuum tubing which leads to a collection vessel is at least equal to the diameter of the first quarter wavelength section. Only a slight increase in bore diameter in the second section is necessary to achieve the desired effect. Excessive over-enlargements are not desired, since they may allow a core of typical length to rotate within the bore and become jammed perpendicular to the long axis of the tip. Generally, the bore need only increase a minimum of one and a maximum of 1000 percent in any defining dimension such as diameter or width and height to satisfactory achieve reduced blockage of the device while avoiding a perpendicular core jam.

Figure 3:
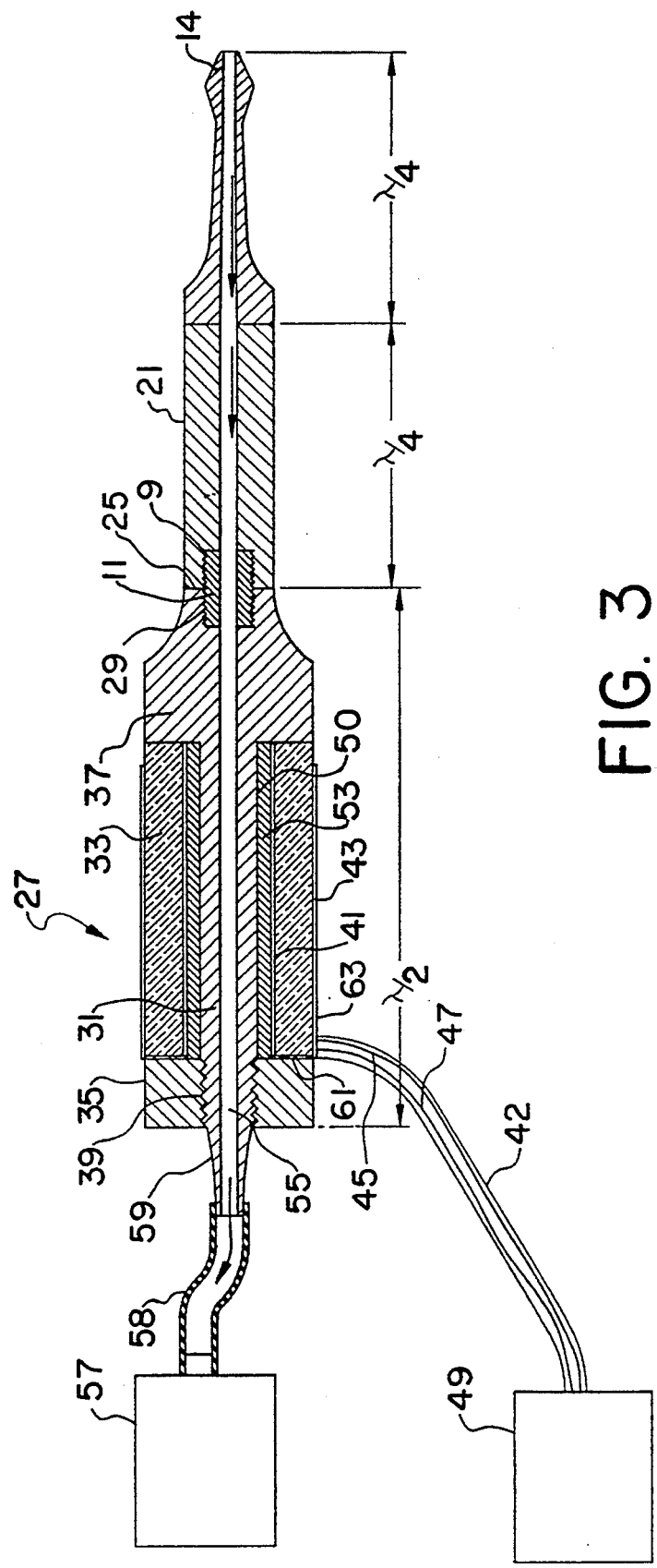
FIG. 3 is a side view, in cross section, of one embodiment of the present invention including the hollow tip illustrated in FIG. 1.
Figure 4:
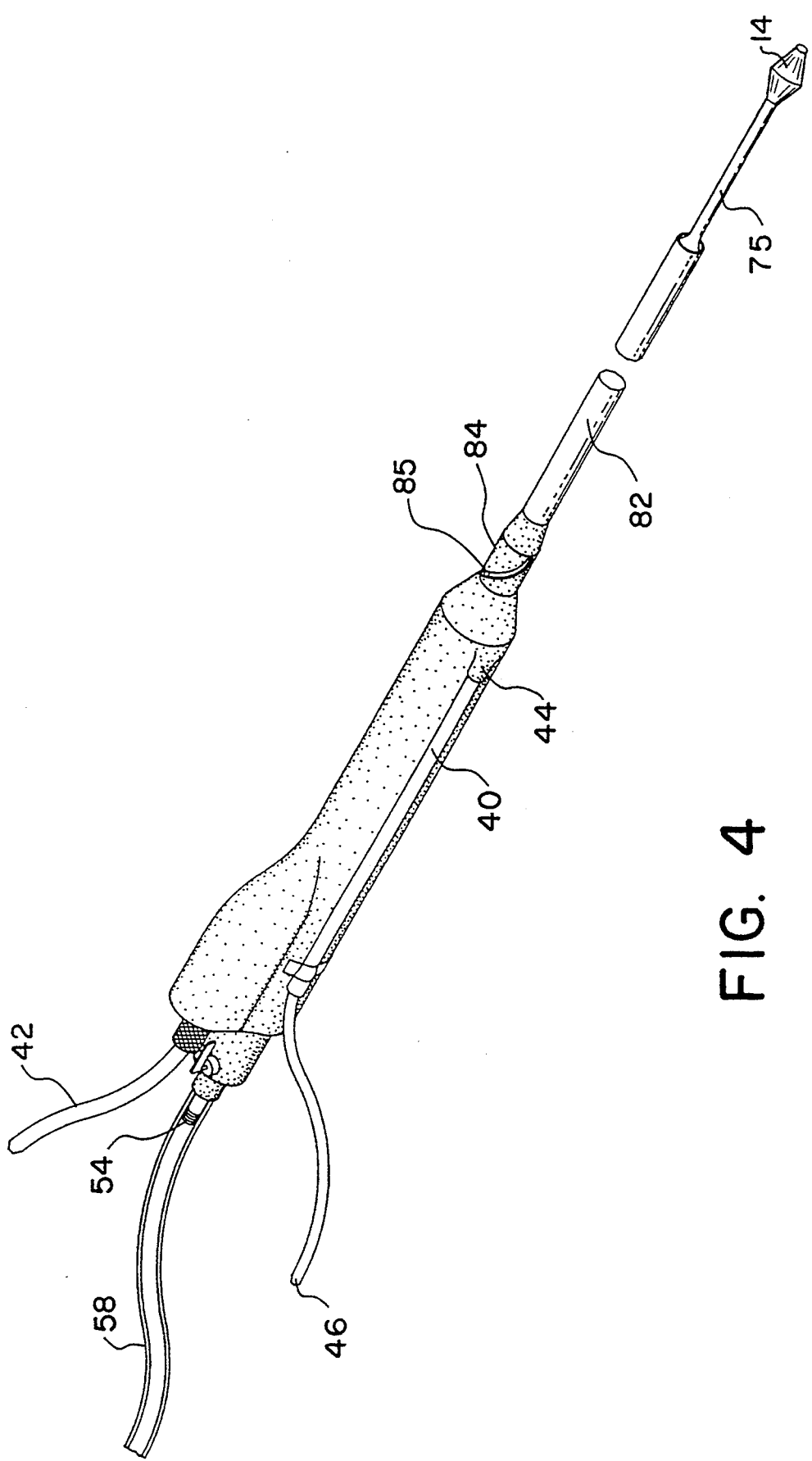
FIG. 4 is a perspective view of the embodiment of FIG. 3.

FIGS. 3 and 4 illustrate an embodiment of the ultrasonic aspirating surgical device of the present invention utilizing the hollow surgical tube illustrated in FIG. 1. The hollow surgical tube is affixed (at the transducer contacting surface 7) to the tube contacting surface 25 of ultrasonic transducer 27 by means of hollow stud 11 mating with the internal threads 29 located within the tube contacting surface of the transducer and the internal threads 9 of the hollow tube.

The transducer illustrated in FIGS. 3 and 4 is comprised of a hollow bolt 31, a hollow cylindrical piezoelectric crystal 33 and a nut 35. The hollow bolt lies within a bore defined by the crystal so that one end of the crystal is positioned adjacent to a cap portion 37 of the hollow bolt. Nut 35 is placed onto external threads 39 of the hollow bolt and tightened so as to compress the hollow cylindrical crystal between the cap portion and the nut. Electrodes 61 and 63 conduct alternating current respectively to internal surface 41 and external surface 43 of the piezoelectric crystal. Wires 45 and 47 located within conduit 42 are used to conduct electricity from a source of alternating current 49 to the electrodes.

As current is applied to the piezoelectric crystal, ultrasonic vibration is produced. The vibration is conducted through the hollow bolt to the hollow surgical tube. The vibration, as described in detail above is sufficient to melt prosthetic cement. However, a great deal of heat is also generated by the piezoelectric crystal. A thermally conducting electrically insulating layer of material 53, such as for example, boron nitride is positioned between the internal surface of the crystal 41 and the external surface of the bolt 50. As heat is liberated from the crystal, the thermally conducting, electrically insulating material conducts the heat from the crystals inner surface to the external surface of hollow bolt 31. Heat is then conducted through the bolt to bore 55 thereby defined. A vacuum pump 57 provides suction via a tube 58 to the ultrasonic device through an external fitting 59 located at a terminus of the hollow bolt 31 extending beyond the nut 35. An irrigation line 40 communicating with an elongated sheet member surrounding the hollow surgical tube via connector 44 provides irrigant to the operative site from an irrigant source 46.

During surgery, the vacuum supplied by pump 57 causes irrigating solution to be aspirated by the surgical tip in the direction of arrow 21. The irrigating solution flows through the bore of the hollow surgical tube, hollow stud, hollow bolt, and tubing, finally entering a collection jar (not shown). As the irrigating solution passes through the hollow bolt, it conducts heat away thereby cooling the bolt and preventing excessive heat build-up in the transducer.

Figure 5:
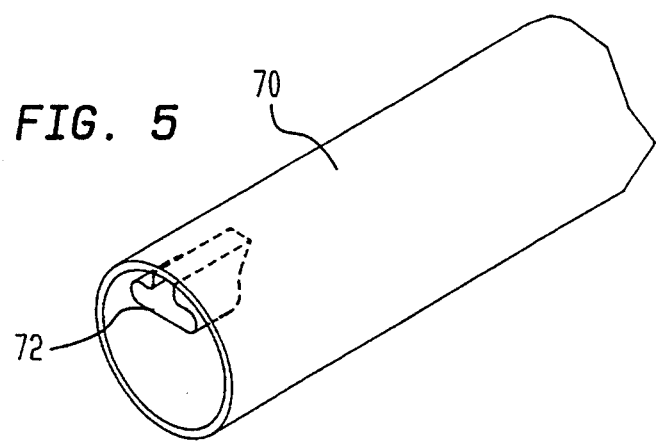
FIG. 5 is an end view of another hollow tip for use in the present invention.
Figure 6:
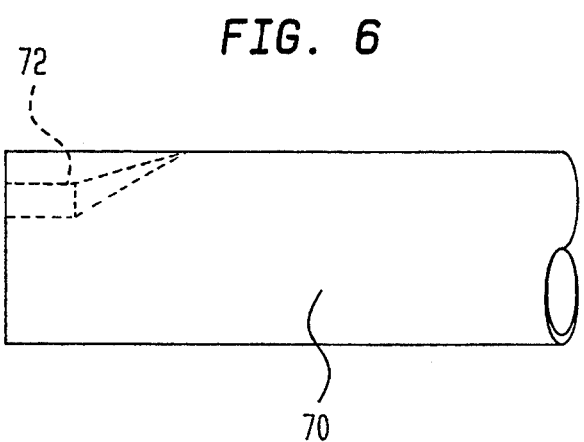
FIG. 6 is a side view, in cross section, of the tip of FIG. 4.

Another embodiment of the tip of the invention is illustrated in FIGS. 5–6. There, the second tube section; 70 includes a notch 72 or key way along a portion of its internal surface proximate the tip. This notch 72 receives cement as the tool is vibrated when contacting bone cement. After the cement is melted and resolidifies within second section 70, the notch portion 72 provides a "lock" onto the cement. Thus, discontinuing the vibration of the tip and application of a rotational force to the handpiece will shear the extracted cement at its pedestal or point of contact with unremoved cement. Suction then will remove the sheared cement through the device as noted above.

Figure 7:
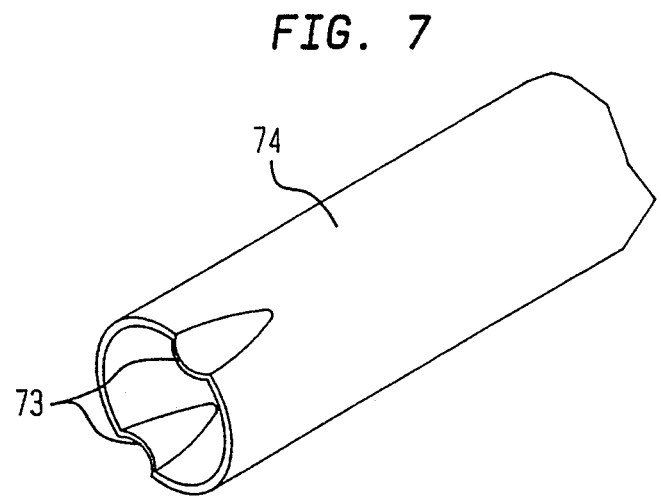
FIG. 7 is an end view of another hollow tip for use in the present invention.

FIG. 7 illustrates still another embodiment of the second section of the hollow surgical tube of the present invention. Second section 74 includes flats 73 along a portion of the internal surface proximate the tip. These flats receive cement as the tool is vibrated when contacting bone cement. After the cement is melted and resolidifies in second section 74, the flats portion 73 provides a "lock" onto the cement. Thus, discontinuing the vibration of the tip and application of a rotational force to the handpiece will shear the extracted cement at its pedestal or point of contact with unremoved cement. Suction then will remove the sheared cement through the device as noted above.

FIGS. 8 and 9 illustrate the irrigation ports and fluid directing means of the invention. In these figures, second section 75 includes a base 77 having four longitudinal grooves 79 oriented 90° apart about the circumference of base 77. An O-ring 80 of conventional elastomeric material slips over but does not block, these grooves 79 and forms a water tight seal with the inner circumference of the forward end of sheath 82.

In FIG. 8, the sheath base 84 is illustrated in a retracted position which is obtained by counterclockwise rotation of the sheath. This allows pin 85 to move to the forward end of slot 86 thus withdrawing the end of sheath 82 away from O-ring 80 and base 77. This allows connection of second section 75 to first section 1, or removal of second section 75 therefrom.

FIG. 9 illustrates the operative assembly of the sheath 82 and second section 75. In this Figure, sheath 82 has been extended by clockwise rotation so that pin 85 is positioned in the furthermost area of slot 86. Thus, O-ring 80 makes a fluid tight seal with the forward end of sheath 82. Thus, irrigation fluid which passes through sheath 82, can exit only through irrigation ports 79, and is directed as a spray toward the surgical tip of second section 75. To prevent fluid pressure form forcing the O-ring away from the sheath, a circumferential O-ring groove (not shown) is provided. Thus, the O-ring is securely retained in position in sealing engagement with sheath 82 as fluid exits through ports 79.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

I claim:

1. A method for removing thermoplastic prosthetic cement from bone comprising:
   contacting thermoplastic prosthetic cement adherent to a bone surface with an aspirating ultrasonically vibrating surgical device, having a centrally located bore which extends throughout the length of said device;
   vibrating said device to provide ultrasonic vibration of a sufficient amplitude and frequency to melt said cement while simultaneously irrigating said bone surface; and
   aspirating said melted cement and irrigant through said bores of said device;
   wherein the distal end of the bore expands in diameter in the direction of aspirant flow to facilitate removal of said melted cement and wherein removal of said irrigant cools heat generated by said device.

2. The method of claim 1 comprising providing said device with a surgical tip and an ultrasonic transducer and vibrating the surgical tip from 50 to 500 microns at a frequency of from 10 to 50 kHz.

3. The method of claim 1 wherein said bore is selected so as to expand in diameter in the direction of aspirant flow from about 1 to 1000 percent.

4. The method of claim 1 wherein said aspirating ultrasonically vibrating device contacts cement adherent to bone cavity surrounding an endoprosthesis so as to remove said endoprosthesis.

5. The method of claim 1 wherein said aspirating ultrasonically vibrating device contacts cement adherent to a bone cavity from which an endoprosthesis has been removed.

6. The method of claim 1 further comprising rotating said device to create a shearing force while said device is vibrating whereby the shearing force and said ultrasonic vibration may be simultaneously applied to said cement.

7. A method for removing thermoplastic prosthetic cement from bone comprising:
   applying ultrasonic vibration to thermoplastic prosthetic cement adherent to a bone surface, wherein said vibration is of a sufficient amplitude and frequency to melt said cement;
   simultaneously irrigating said bone surface; and
   aspirating and removing said melted cement and irrigant.

8. The method of claim 7 wherein the ultrasonic vibration has a frequency of from 10 to 50 kHz.

9. The method of claim 8 further comprising rotating said device to create a shearing force while said device is vibrating whereby the shearing force and said ultrasonic vibration may be simultaneously applied to said cement.

10. The method of claim 7 wherein the aspirating of melted cement and irrigant is conducted through a bore located centrally throughout the length of a device; wherein the distal end of the bore expands in diameter in the direction of aspirant flow to facilitate removal of said melted cement and wherein removal of said irrigant cools heat generated by said device.

11. The method of claim 71 wherein the thermoplastic prosthetic cement is cement adherent to bone cavity surrounding an endoprosthesis.

12. The method of claim 7 wherein the thermoplastic prosthetic cement is cement adherent to a bone cavity from which an endoprosthesis has been removed.

* * * * *